United States Patent [19]

Cravett

[11] Patent Number: 5,400,839
[45] Date of Patent: Mar. 28, 1995

[54] HOME DENTAL HYGIENE APPARATUS

[76] Inventor: Michael T. Cravett, 21300 Glassand Spivey Rd., Robertsdale, Ala. 36567

[21] Appl. No.: 30,622

[22] Filed: Mar. 12, 1993

[51] Int. Cl.[6] ............................................. B67D 5/00
[52] U.S. Cl. .................................... 141/362; 141/357; 141/360; 141/361; 141/354; 222/71; 222/181; 132/314
[58] Field of Search ............... 141/351, 354, 355, 357, 141/360, 361, 362, 85; 222/71, 181, 96, 93, 106, 192; 132/308, 309, 310, 314

[56] References Cited

U.S. PATENT DOCUMENTS

| | | | |
|---|---|---|---|
| 1,841,275 | 1/1932 | Baptiste | 141/362 X |
| 2,079,364 | 5/1937 | Stewart | 141/362 |
| 2,231,889 | 2/1941 | Davis | 141/362 |
| 2,570,755 | 10/1951 | Booth | 141/362 |
| 2,623,659 | 12/1952 | Gadelius | 141/362 X |
| 2,792,856 | 5/1957 | Coppage | 141/362 |
| 3,347,288 | 10/1967 | Rutherford | 141/362 |
| 3,417,902 | 12/1968 | Mirka | 141/362 X |
| 3,987,932 | 10/1976 | Maldon | 222/93 X |
| 4,269,238 | 5/1981 | Iwamoto | 141/362 |
| 4,303,110 | 12/1981 | Chen | 141/362 |
| 4,508,239 | 4/1985 | Rozzen | 222/96 X |
| 4,508,240 | 4/1985 | Arango | 222/96 |
| 4,827,951 | 5/1989 | Grussmark | 132/314 |
| 5,215,218 | 6/1993 | Choi | 141/362 X |
| 5,228,595 | 7/1993 | Booker | 222/192 X |

FOREIGN PATENT DOCUMENTS

119306  7/1947  Sweden ............................ 141/357

*Primary Examiner*—Ernest G. Cusick
*Attorney, Agent, or Firm*—Davis C. Holden

[57] ABSTRACT

An improved dental hygene center utilizing push button toothpaste dispenser and incorporating a cooperating floss dispenser, automatic paste dispersal on the brush, mouthwash access, counter for replacement of toothpaste and message center.

13 Claims, 3 Drawing Sheets

HOME DENTAL HYGIENE APPARATUS

BACKGROUND OF THE INVENTION

This invention pertains to toothpaste dispensers. More particularly, this invention pertains to toothpaste dispenser which automatically dispense tooth paste.

1. Prior Art

Several automatic toothpaste dispensers are shown in the prior art.

The prior art shows several mechanisms for obtaining toothpaste from tubes and typically involve the transfer of a compression device along the length of a tube or other mechanism for dispensing paste.

The prior art does not uniformly allow for control of the dispensing, ease of replacement of tubes, even distribution on a brush, and enhanced dental care required in conjunction with dental floss.

2. General Discussion of the Invention

The present invention seeks to improve on the prior art by providing in conjunction with a toothpaste dispenser an automatic feed for the toothbrush, a counter for determining the amount of toothpaste remaining and cooperating dispensers for set amounts of dental floss or mouthwash.

In this way, the invention regulates the amount of toothpaste used and evenly distributes it on the brush and also provides in one location all of the items necessary for normal dental hygiene.

Certain novelty aspects of the invention would also enhance brushing and flossing by a user.

In connection therewith the invention incorporates a trigger which is activated when a toothbrush head contacts with it.

A slide is provided which guides the toothbrush to the trigger mechanism. The trigger mechanism is connected to a driving means designed to push the toothbrush along the guide means which operates in conjunction with a push means which serves to push toothpaste in contact with the toothbrush so that after the toothbrush is pushed against the trigger it is pushed away from the trigger and toothpaste is evenly deposited on the toothbrush.

The mechanism described above is designed to automatically shut off after the appropriate amount of toothpaste is deposited.

In addition, for each cycle of the push means a tracking means which is preferably a counter determines the number of brushes utilized which allows for the user to determine how much toothpaste is left and to make sure that, in fact, everyone has used the device even if everyone failed to brush their teeth after utilizing the device.

In addition, the mechanism could be designed so that each of the several different toothbrushes would disburse a differing amount of toothpaste to be preset by the user.

In connection with that an improvement of the invention would provide multiple counters for each of several users which could be triggered depending on the toothbrush used in order to determine the number of times each user is using the toothbrush.

In addition, there is a line feeder which is designed to feed a predetermined amount of dental floss which can be in the preferred embodiment varied by the user and in the preferred embodiment may be able to be preset for several different users who use different amounts of dental floss.

It is therefore an object of the invention to provide a mechanism to simplify the use of toothpaste and to automatically dispense toothpaste onto a toothbrush.

It is an additional object of the invention to provide a means for providing for several different toothbrushes from a single source the predetermined amount of toothpaste.

It is an additional object of the invention to provide a means for providing from a single source the predetermined amount of dental floss.

It is another object of the invention to allow a user to track how many times a group of users or one individual user utilizes a toothbrush or toothpaste.

Other objects and advantages of the invention will become better understood hereinafter from a consideration of the specification with reference to the accompanying drawings forming part thereof, and in which like numerals correspond to parts throughout the several views of the invention.

DETAILED DISCUSSION OF THE PREFERRED EMBODIMENT(S)

Figure 1:
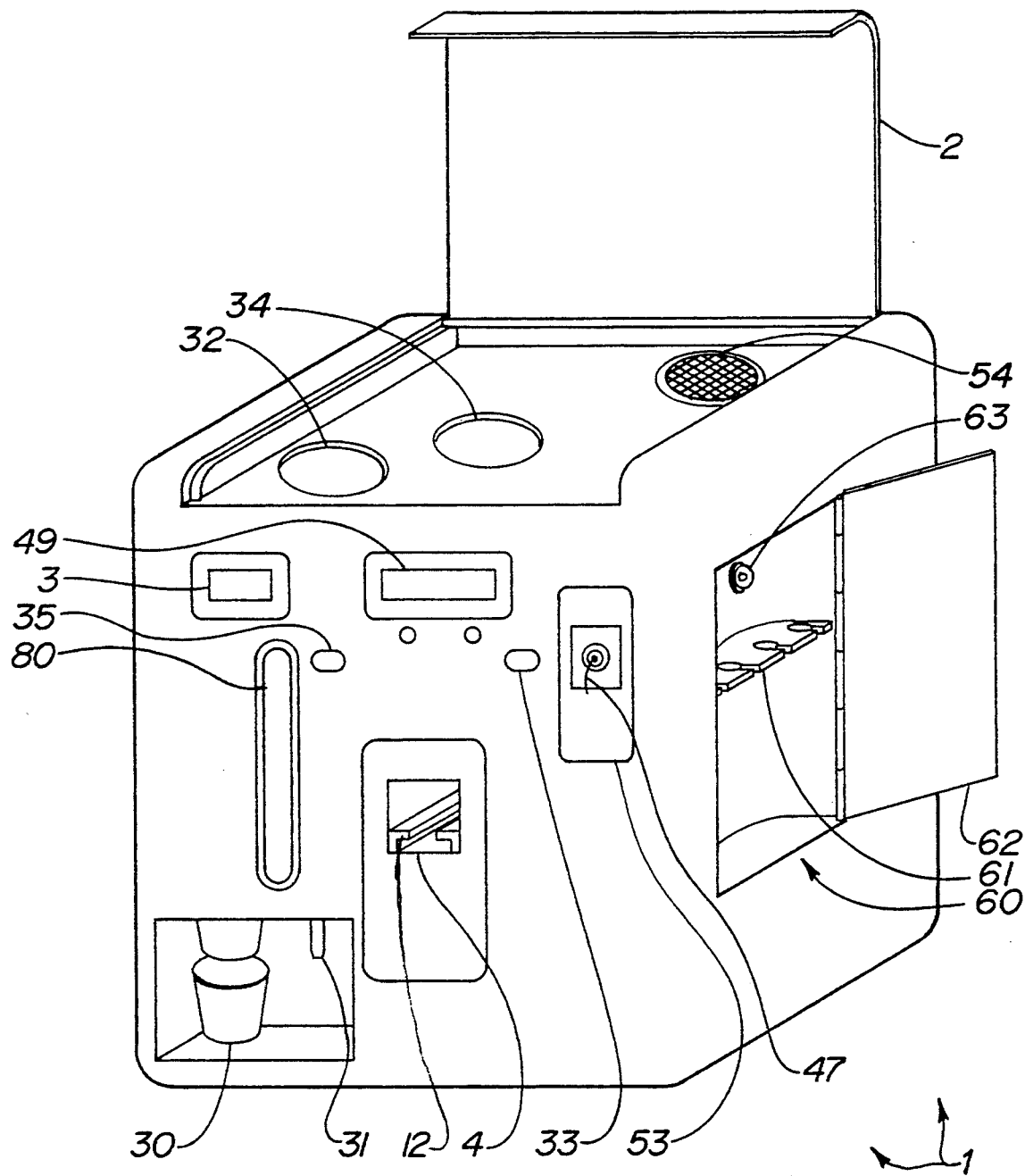
FIG. 1 is a perspective view of the container showing the various openings.
2.

Referring to FIG. 1, it can be seen that the container 1 comprises a access panel 2 which may be lifted to obtain access to the interior, a counter 3, tooth brush opening 4; floss dispenser 5 having a floss opening 6 and floss cutter 7.

The counter 3 may be adjusted to show the number of remaining applications available from the tube. In the preferred embodiment, this counter is preset to show 92 remaining uses whenever a tube of tooth paste is inserted into tube opening 34.

There is a cup dispenser 29 for dispensing cups 30. Also present is a window 80 for observing the level of the mouthwash. A tap 31 for dispensing mouthwash is adjacent to the cups. A refill access 32 is accessible when the access panel 2 is lifted.

Tap 31 is activated by tap button 35. Floss activation button 33 activates the dispensing of floss in addition to automatic dispensing as set forth in more detail below.

FIG. 2, 3, 4 and 5 show the internal workings of the dispenser 1.

Figure 2:
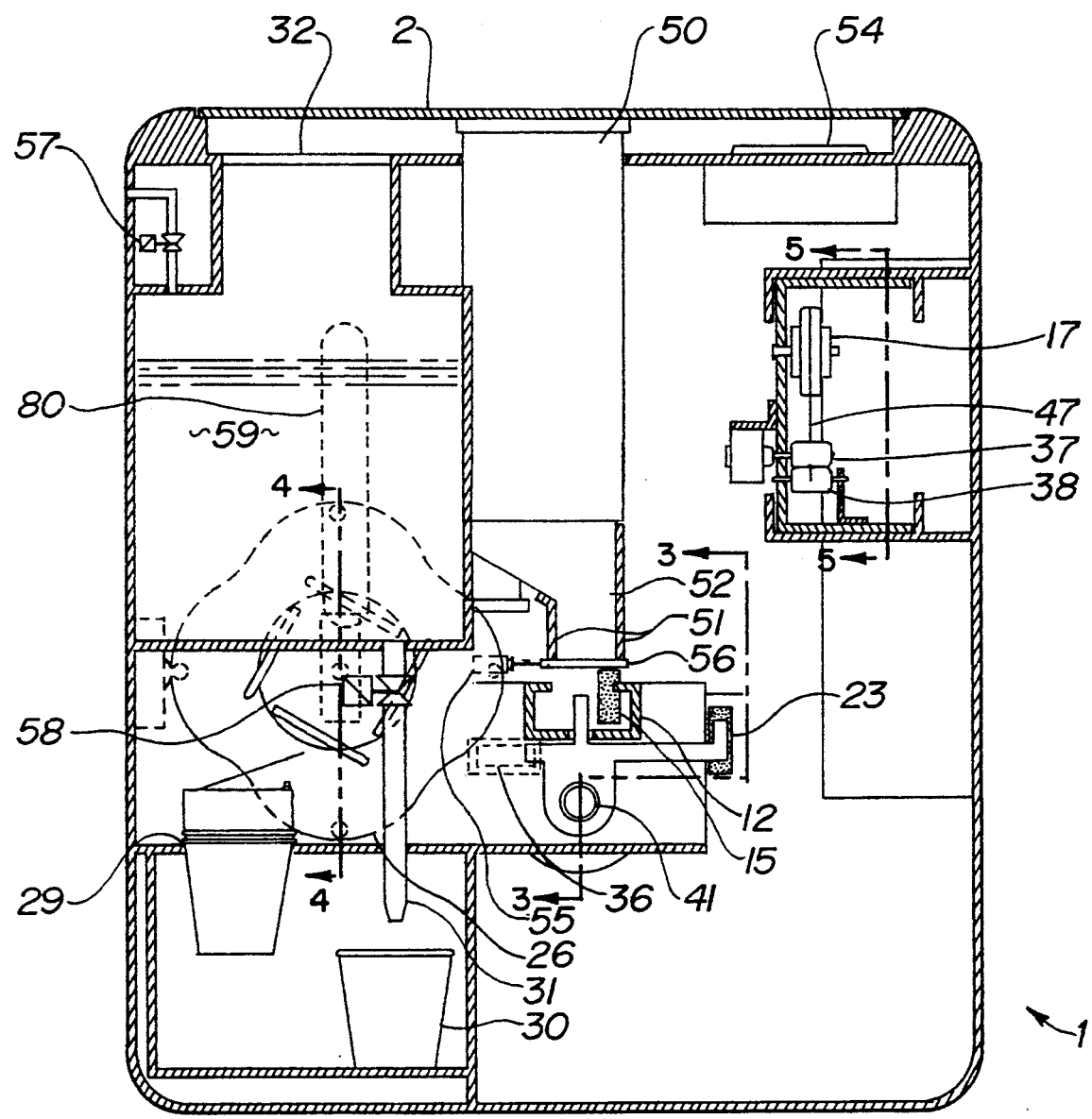
FIG. 2 is a cross sectional view of the invention of FIG. one through the A—A axis.
3.

As can be seen by reference to FIG. 2 the tooth paste 14 is dispensed from tube 13 which sits upside down after being inserted in the top access panel 2 into holder or opening 34 and held by way of brackets 9 and the closing of access panel 2.

Tabs 28 contact wheel 25 which may turn a manual counter.

Gear 24 controls the amount of compression time on the pump stem or handle 11 of a standard pump type dispenser 50 as is known in the art. Gear knobs 16 of gear 24 actually contact the pump stem 11. The level of gear 24 may move up or down approximately 4 millimeters on a track 19 in order to vary the amount of tooth paste dispensed.

FIG. 2 shows a solenoid 55 which controls a cover 56. This cover 56 at when the solenoid 55 is not activated covers the opening of the tube 50. When motor 26 is in operation, the same circuit also activates the solenoid 55 which pulls the cover 56 away from the opening of the tube 50 to allow the paste out. The cover 56 operates to keep the tube 50 sealed when not in use.

FIG. 2 also shows solenoid valves 57 and 58. When tap button 35 is operated each of these two valves 57 and 58 open in order to allow the mouthwash held in reservoir 59 to pass out of the tap 31.

Figure 3:
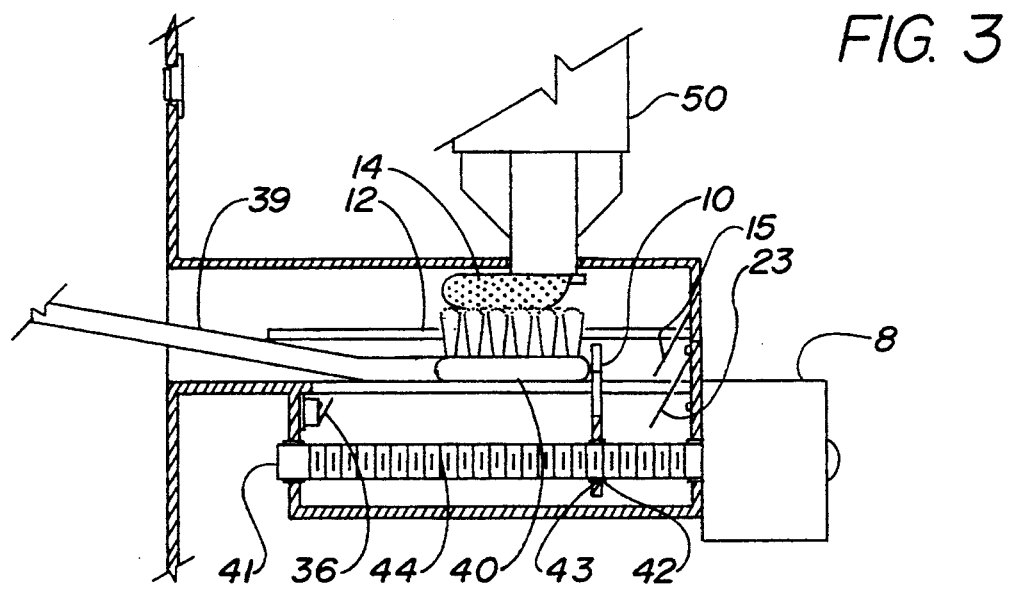
FIG. 3 is a detailed view of the dispenser mechanism shown perpendicular to the view in FIG. 2.
4.
Figure 4:
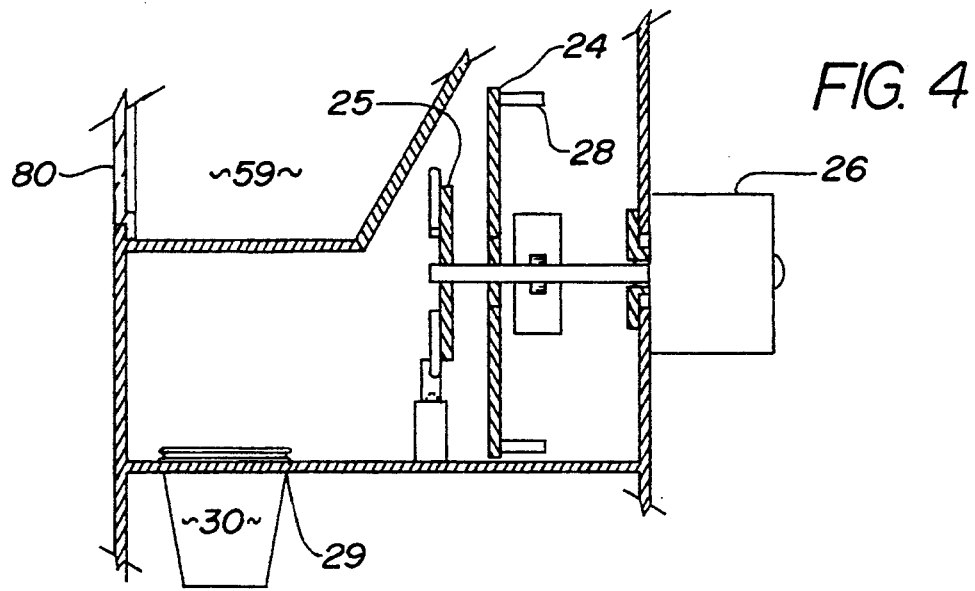
FIG. 4 is a detail view of the gear mechanism shown perpendicular to the view in FIG. 2.
5.
Figure 5:
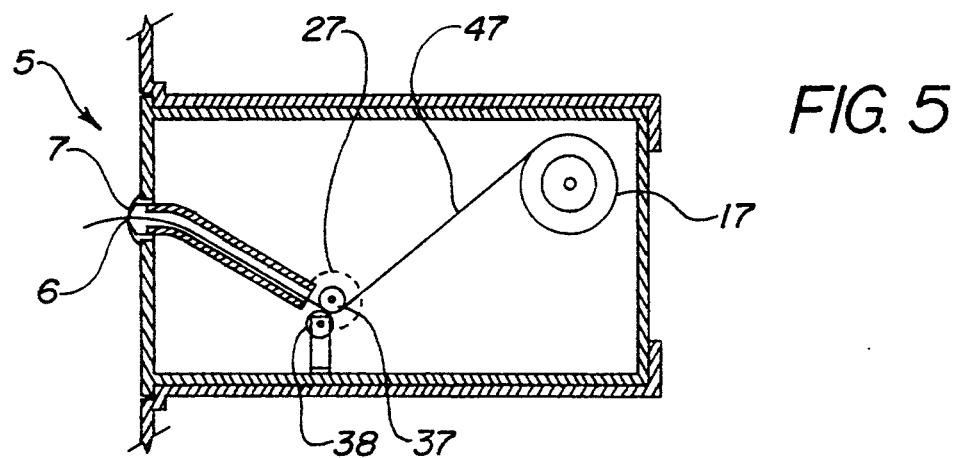
FIG. 5 is a detail view of the floss dispensing mechanism shown perpendicular to the view in FIG. 2.

As can best be seen by reference to FIG. 3 and 4, initial switch 15 initiates the action of motor 26 and motor 8. The motor 26 which drives the gears 24 and 20 is driven by the same circuit operating motor 8. Motors 26 and 8 can be of the same type and are typically 9 volt motors.

The circuit activating motors 26 and 8 are powered when a toothbrush 39 is inserted pushing toothbrush 39 which rests in part against stop 10 into activating switch 15. A gap is provided in stop 10 which the brush head 40 fills so that only when a brush 39 is inserted is switch 15 contacted.

When switch 15 is contacted, motors 26 and 8 are started and continue to run until the circuit is broken by circuit breaking switch 23.

A slide 12 is provided which guides the toothbrush 39 to the switch 15. The switch 15 controls motor 8 which operates a screw type driving means 41 designed to push the toothbrush 39 along the guide means 12 as the screw 41 turns. Stop 10 contains a threaded bearing 42 which is rotatably held in a fixed location within stop 10 and has threads 43 which match thread 44 on screw type drive 41. In this way, as drive 41 turns, the stop 10 is moved forward or backwards depending on the direction of the turning of the screw type drive 41.

A stand 21 external to the dispenser may be placed in order to allow for heavier toothbrushes such as electric models so that the guide is essentially extended to allow for the electric models to be used with the dispenser.

Drive 41 and stop 10 operate as a push means which serves to push the toothbrush beneath the toothpaste tube 13 so toothpaste is evenly deposited on the toothbrush 39 as shown in FIG. 3.

The activation of motor 8 is reversed when stop 10 pushes against reversing switch 36. This is designed so the dispensing of tooth paste is simultaneously stopped or stopped sooner than reversing of stop 10 so that tooth paste is not wasted. When reversing switch 36 is contacted, the motor 8 runs backwards and the circuit to motor 26 is cut. This prevents accidental wasting of toothpaste and moves the stop 10 back toward the initiating switch 15. The activation of motor 8 is terminated when stop 10 contacts circuit breaking switch 23.

As Motor 8 turns screw drive 9 which in turning screws the toothbrush stop 10 the toothbrush is pushed back out of the dispenser. Although the invention thus described operates to dispense a given amount of paste on a standard type of brush, it can be seen that utilizing this the amount of paste dispensed and the timing thereof can be controlled by affecting the length of time knobs 26 contact pump stem 52 so that the invention can be made to work with any number of toothbrushesdin any of several appearances.

In addition, as shown in FIGS. 1 and 3, for each cycle of the push means, which is comprised of drive 41 and stop 10, a tracking means which is preferably a counter 3 determines the number of times the invention is utilized which allows for the user to determine how much toothpaste is left and to make sure that, in fact, everyone has used the device.

As the use of dental floss is avoided by many users, the invention incorporates an important improvement which may operate in conjunction with the paste dispenser to enhance the use of dental floss.

As can best be seen by reference to FIGS. 2 and 4, a third motor shown as 27 on FIG. 2 drives a floss roller 37 which by turning against a fixed roller 38 guides floss 47 through floss opening 6. Motor 27 is turned on and off in the preferred embodiment alternatively by either a manual switch 33 or activation of reversing switch 36 of the motors 8. In this way, when a user desires, he may shut off the dispensing of dental floss or have floss dispensed at will. However, when users of the device are recalcitrant to use dental floss, reversing switch 36 may be set to automatically, activate motor 27 so that dental floss is automatically dispensed in an preset amount. In this way, the user is forced to remove the dental floss and use it or discard it or ignore its presence as dispensed. Since it is well known in the art that the use of dental floss is important in the prevention of gum disease, this is a very significant improvement over the prior art. If the amount of floss dispensed automatically is insufficient, the manual dispensing button 33 may be used to operate manually motor 27 to augment the amount of floss dispensed.

Floss wheel 17 may be accessed through access door 53 shown in FIG. 1 for changing or stringing floss through wheels 18 and 32.

An additional chamber 48 holds mouthwash. This allows for a set amount to be dispensed by the user automatically based on the operation of a two solenoids 45 and 46 using switch 35.

FIG. 1 shows several other cooperating features. First, a recorder 54 with pre-recorded messages on hygene is triggered by operation of switch 15. This causes one of several different messages on hygene to be played.

The container 1 also comprises a toothbrush holder 60 which closes with a cover 62. Racks 61 hold tooth brushes (not shown) below an ultraviolet light 63. Light 63 is operated for a set period of time by the closing of cover 62. It may also be set to automatically turn on whenever a set amount of time passes on the clock 49. The purpose of this light is to reduce bacteria growth on the brushes.

I claim:

1. A home dental hygiene apparatus, including a toothpaste dispenser for evenly dispensing toothpaste from a tube and comprising:
   (a) a toothpaste holder and a means for dispensing toothpaste from the holder at a dispensing location within the dispenser;
   (b) a guide means for positioning movably a toothbrush below the dispensing location, wherein said guide means includes a tooth brush guide to receive and movably guide an inserted tooth brush along a set linear path below the dispensing location and an activating switch located within the guide which activates the movement of the toothbrush in the guide when the toothbrush touches the activating switch;
   (c) an activating means for operating the guide means in conjunction with the dispensing means so that the toothbrush bristles are moved below the dispensing locations as the dispensing means dispenses toothpaste; and, (d) a floss container, a floss dispenser, and a floss dispensing switch, said floss dispensing switch having a setting means for automatically activating said floss dispenser upon activation of said toothpaste dispensing means so that floss is made to automatically dispense and also a means for regulating the amounts of paste and floss.

2. The invention of claim 1 wherein the floss dispenser further comprises:

(i) a feed wheel;

(ii) a motor driving said feed wheel attached to the container and activated by the floss activating means;

(iii) a friction wheel contacting the feed wheel so that floss may be fed between the friction wheel and the feed wheel; and, (iv) a spool holding floss located adjacent to the feed wheel so that the floss from the spool may be fed between the friction wheel and the feed wheel.

3. The invention of claim 2 wherein the floss activating means is automatically activated by the operation of the activating means.

4. A home dental hygiene apparatus including a toothpaste dispenser for evenly dispensing toothpaste from a tube and comprising:

(a) a toothpaste holder and a means for dispensing toothpaste from the holder at a dispensing location within the dispenser;

(b) a guide means for positioning movably a toothbrush below the dispensing location, wherein said guide means includes a tooth brush guide to receive and movably guide an inserted tooth brush along a set linear path below the dispensing location and an activating switch located within the guide which activates the movement of the toothbrush in the guide when the toothbrush touches the activating switch;

(c) an activating means for operating the guide means in conjunction with the dispensing means so that the toothbrush bristles are moved below the dispensing locations as the dispensing means dispenses toothpaste;

(d) a counter for recording the number of times the dispensing means operates and displaying the approximate number of remaining uses or the number of times used.

5. A home dental hygiene apparatus including a toothpaste dispenser for evenly dispensing toothpaste from a tube and comprising:

(a) a toothpaste holder and a means for dispensing toothpaste from the holder at a dispensing location within the dispenser;

(b) a guide means for positioning movably a toothbrush below the dispensing location, wherein said guide means includes a tooth brush guide to receive and movably guide an inserted tooth brush along a set linear path below the dispensing location and an activating switch located within the guide which activates the movement of the toothbrush in the guide when the toothbrush touches the activating switch;

(c) an activating means for operating the guide means in conjunction with the dispensing means so that the toothbrush bristles are moved below the dispensing locations as the dispensing means dispenses toothpaste;

(d) a mouthwash dispenser, said dispenser including, a reservoir for containing mouthwash, a tube leading to the outside from said reservoir, at least one solenoid valve located along the tube for controlling the flow of mouthwash through the tube, and a means for energizing the solenoid valve.

6. The invention of claim 5 wherein the energizing means is activated by the activating means.

7. A home dental hygiene apparatus including a toothpaste dispenser for evenly dispensing toothpaste from a tube and comprising:

(a) a toothpaste holder and a means for dispensing toothpaste from the holder at a dispensing location within the dispenser;

(b) a guide means for positioning movably a toothbrush below the dispensing location, wherein said guide means includes a tooth brush guide to receive and movably guide an inserted tooth brush along a set linear path below the dispensing location and an activating switch located within the guide which activates the movement of the toothbrush in the guide when the toothbrush touches the activating switch;

(c) an activating means for operating the guide means in conjunction with the dispensing means so that the toothbrush bristles are moved below the dispensing locations as the dispensing means dispenses toothpaste;

(d) a toothbrush holder having brackets to hold toothbrushes, an ultraviolet light attached to the container and a timer wherein the light is activated when a toothbrush is replaced for a period of time controlled by the timer.

8. The invention of claim 7 further comprising a clock and wherein the ultraviolet light is further activated whenever a given period of time has passed on the clock, thereby reducing bacteria growth on the toothbrushes.

9. A home dental hygiene apparatus including a toothpaste dispenser for evenly dispensing toothpaste from a tube and comprising:

(a) a toothpaste holder and a means for dispensing toothpaste from the holder at a dispensing location within the dispenser;

(b) a guide means for positioning movably a toothbrush below the dispensing location, wherein said guide means includes a tooth brush guide to receive and movably guide an inserted tooth brush along a set linear path below the dispensing location and an activating switch located within the guide which activates the movement of the toothbrush in the guide when the toothbrush touches the activating switch;

(c) an activating means for operating the guide means in conjunction with the dispensing means so that the toothbrush bristles are moved below the dispensing locations as the dispensing means dispenses toothpaste;

(d) at least one toothpaste tube bracket for receiving a pump type toothpaste tube dispenser, said dispenser having a pump stem;

(e) a stop defining a first space which may be filled by a toothbrush head which first space is sufficiently narrow so as to engage a portion of the toothbrush head and wherein said activating switch is positioned on one end of said guide and is positioned within said first space defined by said stop so that said toothbrush head contacts said activating switch when it is inserted against said stop and said stop further defining a second space for receiving a rotating bearing;

(f) a rotating threaded bearing fitting within the space defined by the stop for receiving a rotating bearing;

(g) a motor activated by the activating switch;

(h) a screw drive means driven by the motor for turning the threaded bearing and moving the stop along the guide thereby moving the toothbrush along the guide;

(i) a reversing switch lying within the line of travel of the stop along the guide so that when the stop reaches the reversing switch it activates the reversing switch which reverses the direction of the screw drive and moves the stop back toward the activating switch; and, (j) a deactivating switch lying with the line of travel of the stop so that when the stop moves toward the activating switch it contacts the deactivating switch turning off the motor.

10. A home dental hygiene apparatus including a toothpaste dispenser for evenly dispensing toothpaste from a tube and comprising:

(a) a toothpaste holder and a means for dispensing toothpaste from the holder at a dispensing location within the dispenser;

(b) a guide means for positioning movably a toothbrush below the dispensing location, wherein said guide means includes a tooth brush guide to receive and movably guide an inserted tooth brush along a set linear path below the dispensing location and an activating switch located within the guide which activates the movement of the toothbrush in the guide when the toothbrush touches the activating switch;

(c) an activating means for operating the guide means in conjunction with the dispensing means so that the toothbrush bristles are moved below the dispensing locations as the dispensing means dispenses toothpaste;

(d) a pump motor activated by the activating means; and, (e) a gear connected to the pump motor and rotated thereby, wherein said gear defines at least one gear tooth which is in close proximity to a pump stem of said toothpaste tube along its circumference of rotation so that when the pump motor turns the gear at least one gear tooth contacts said pump stem depressing said pump stem for the period of time where the gear tooth contacts said pump stem.

11. The invention of claim 10 wherein the gear further comprises a slot for movement up and down of the gear so as to control the length of time during which said gear contacts the pump stem.

12. The invention of claim 10 wherein dispensing means further comprises a counter switch which is in contact with the said gear and is activated by the rotation of the gear to advance the counter.

13. A home dental hygiene apparatus including a toothpaste dispenser for evenly dispensing toothpaste from a tube and comprising:

(a) a toothpaste holder and a means for dispensing toothpaste from the holder at a dispensing location within the dispenser;

(b) a guide means for positioning movably a toothbrush below the dispensing location, wherein said guide means includes a tooth brush guide to receive and movably guide an inserted tooth brush along a set linear path below the dispensing location and an activating switch located within the guide which activates the movement of the toothbrush in the guide when the toothbrush touches the activating switch;

(c) an activating means for operating the guide means in conjunction with the dispensing means so that the toothbrush bristles are moved below the dispensing locations as the dispensing means dispenses toothpaste;

(d) a cover and a solenoid, wherein said cover is controlled by said solenoid which cover fits over the mouth of the toothpaste tube and wherein the solenoid pulls the cover away from the tube when energized and wherein the activating means energizes the solenoid.

* * * * *